US00PP23373P3

(12) United States Plant Patent
Deng et al.

(10) Patent No.: US PP23,373 P3
(45) Date of Patent: Jan. 29, 2013

(54) ***GERBERA* PLANT NAMED 'UFGE 7014'**

(50) Latin Name: *Gerbera hybrida*
Varietal Denomination: UFGE 7014

(75) Inventors: Zhanao Deng, Riverview, FL (US); Brent K. Harbaugh, Bradenton, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 85 days.

(21) Appl. No.: 12/931,609

(22) Filed: Feb. 4, 2011

(65) Prior Publication Data

US 2012/0204302 P1 Aug. 9, 2012

(51) Int. Cl.
*A01H 5/00* (2006.01)

(52) U.S. Cl. ..... Plt./357

(58) Field of Classification Search ..... Plt./357
See application file for complete search history.

*Primary Examiner* — June Hwu

(57) ABSTRACT

A new *Gerbera* plant particularly distinguished by having a novel combination of medium lengths of peduncles, semi-double bright white flower color, an overall inflorescence diameter of approximately 11 cm, a moderate level of resistance to powdery mildew, and demonstrated potential to produce attractive plants in large (≧20-cm in diameter) containers, is disclosed.

3 Drawing Sheets

Genus and species: *Gerbera hybrida.*
Variety denomination: 'UFGE 7014'.

BACKGROUND OF THE NEW PLANT

The invention relates to a new and distinct variety of *Gerbera hybrida* plant named 'UFGE 7014'. 'UFGE 7014' originated from a cross made at in Wimauma, Fla. in 2005 between the female parent, 'Sunburst Snow White' (unpatented), and the male parent, 'UFGE 4033' (unpatented), an unreleased breeding line selected in Bradenton, Fla. in 2004 from a population of progeny of the cross 'UFGE 31-19' (unpatented) and 'UFGE 35-4' (unpatented). 'UFGE 7014' was selected by the inventors from the progeny of the stated parentage in summer 2007 in Wimauma, Fla. The first asexual reproduction of 'UFGE 7014' was done by crown division in fall 2007 in Wimauma, Fla.; and subsequent asexual reproduction was through tissue culture. Plants of 'UFGE 7014' have been asexually propagated by crown division and tissue culture for more than three generations. Asexually propagated plants of 'UFGE 7014' have remained true to the original selected plant, and all characteristics of the plant have been transmitted and retained through three successive asexual vegetative generations.

Plant Breeder's Rights for this cultivar have not been applied for. 'UFGE 7014' has not been made publicly available more than one year prior to the filing of this application.

SUMMARY OF THE INVENTION

The new and distinct variety of *Gerbera* plant is characterized by a novel combination of medium lengths of peduncles, semi-double bright white inflorescences, an overall inflorescence diameter of approximately 11 cm, a moderate level of resistance to powdery mildew, and demonstrated potential to produce attractive plants in large (≧20-cm in diameter) containers. 'UFGE 7014' has not been observed under all possible environmental conditions. Its phenotype may vary significantly with variations in environment such as light intensity, temperature, and day length. The following are the most outstanding and distinguishing characteristics of this new cultivar when grown in Wimauma, Fla. under normal horticultural practices in greenhouse conditions which closely approximate those generally used in commercial practice.

1. Peduncle length of approximately 42 cm;
2. Semi-double inflorescence type;
3. White (RHS 155D) ray florets;
4. Yellow-green (RHS 154C) color discs before opening of disc florets;
5. White (RHS 155B) perianth lobe of disc florets;
6. Inflorescence diameter of approximately 11 cm; and
7. Moderate resistance to powdery mildew.

DESCRIPTION OF THE PHOTOGRAPHS

This new *Gerbera* plant is illustrated by the accompanying photographs which show the plant's form, inflorescence, and foliage. The colors shown are as true as can be reasonably obtained by conventional photographic procedures. The photographs are of a plant approximately 3 months old which was produced from one tissue culture liner and is potted in a 2.7-L container. Colors in the photograph may differ slightly from the color values cited in the detailed botanical description, which accurately describe the colors of the new *Gerbera.*

DESCRIPTION OF THE NEW CULTIVAR

Figure 1:
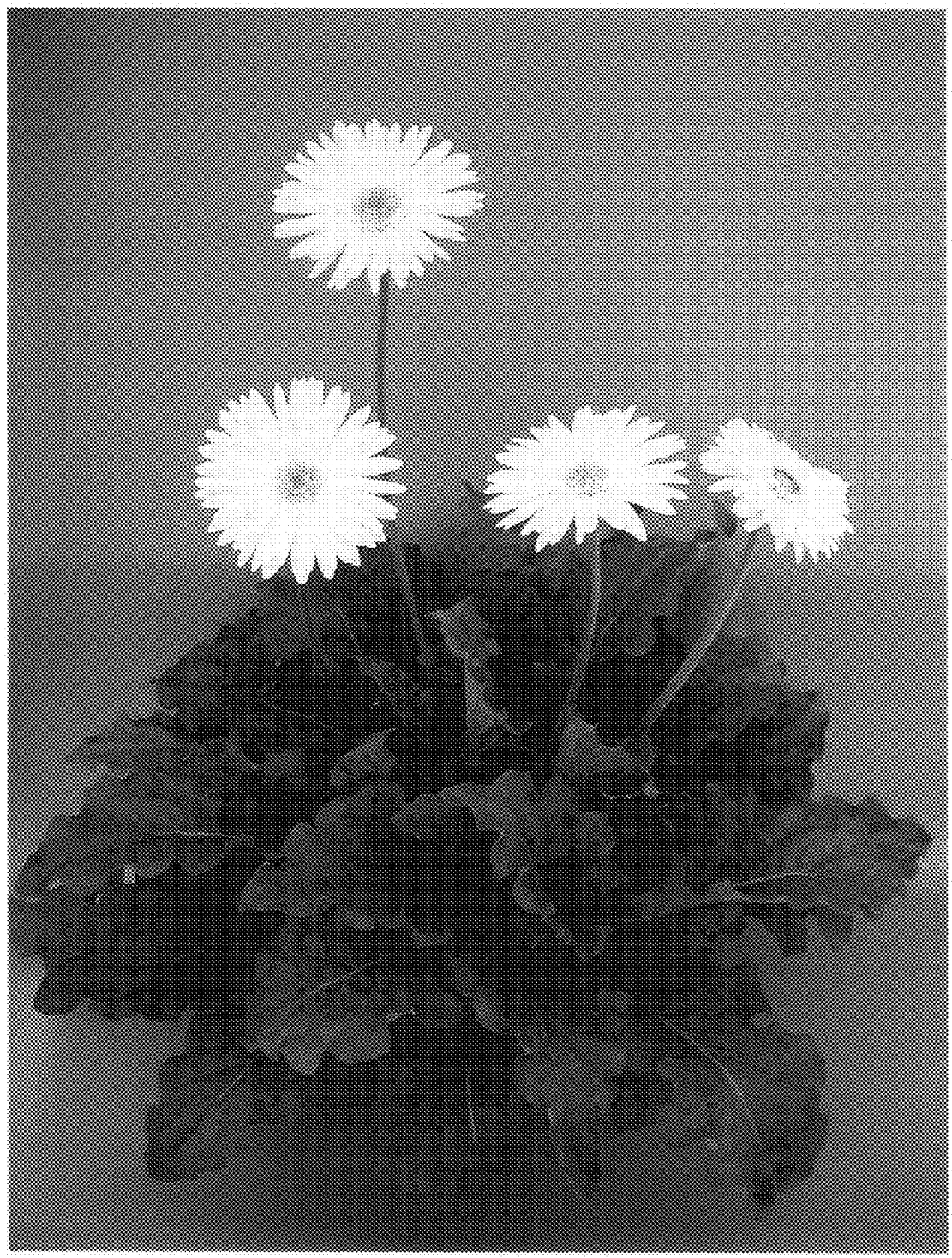
FIG. 1 shows the overall plant habit including inflorescences and foliage and is taken from a side perspective view.
Figure 2:
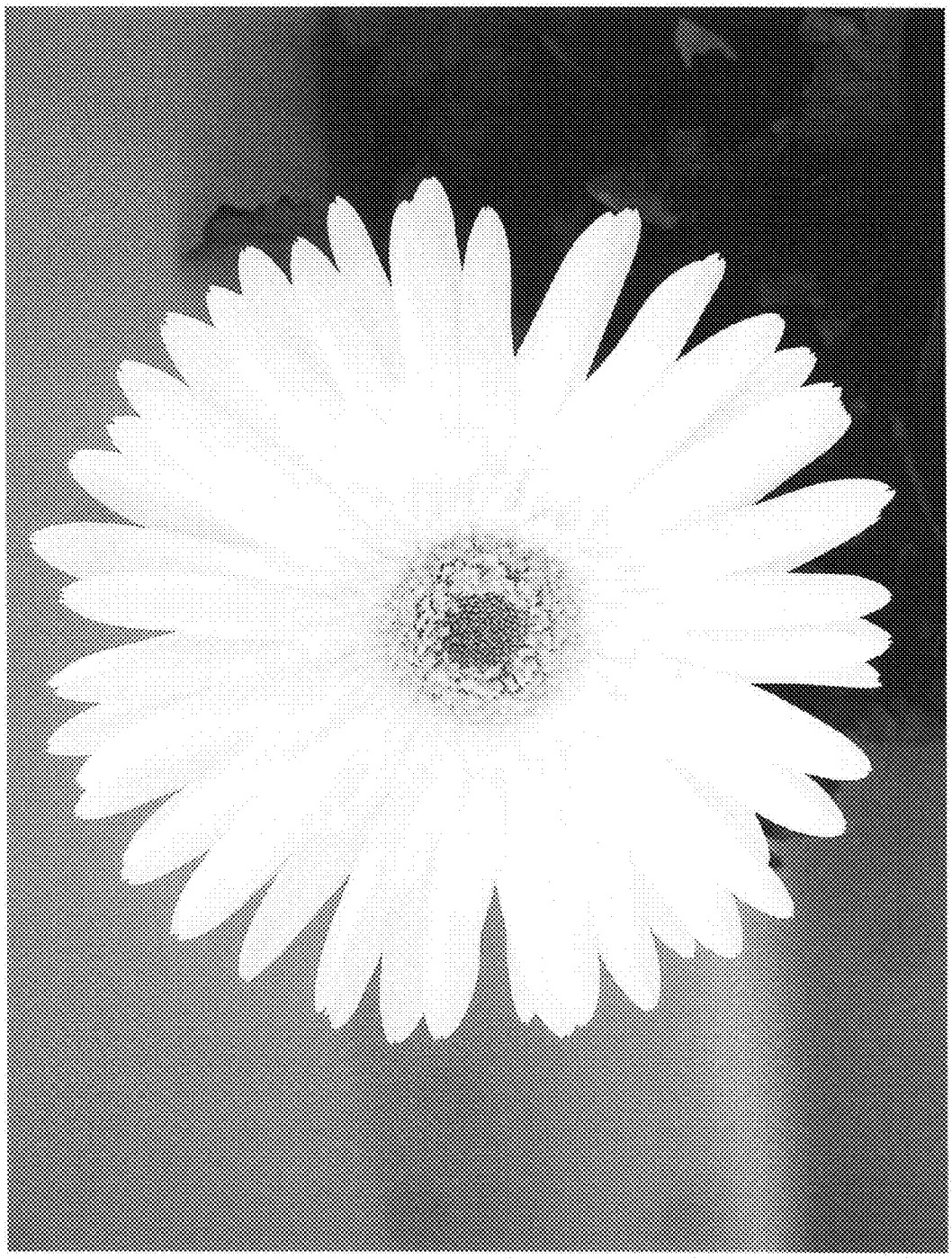
FIG. 2 shows a close-up of the inflorescence head.
Figure 3:
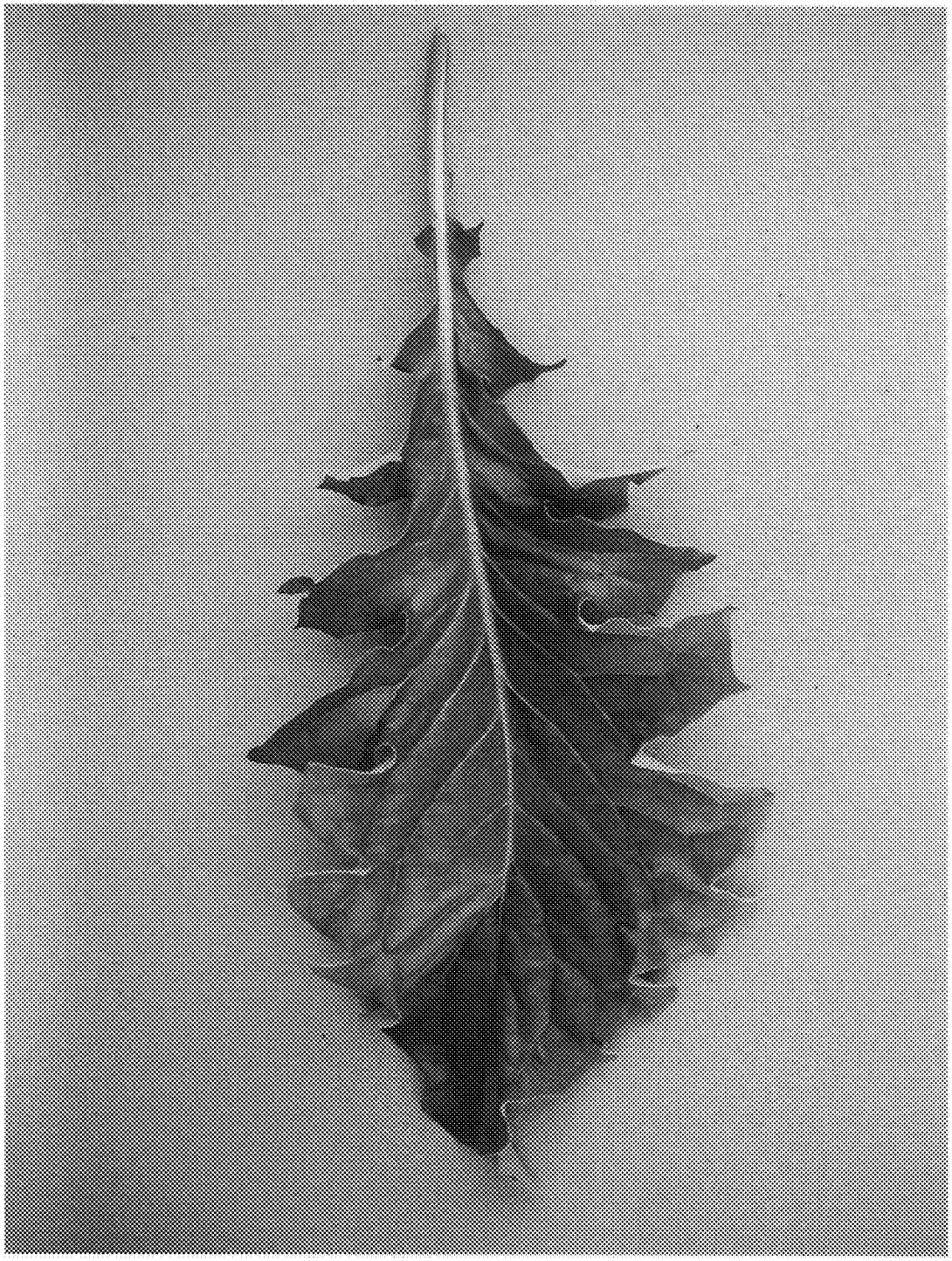
FIG. 3 shows a close-up of the typical leaf.

The following detailed description sets forth the distinctive characteristics of 'UFGE 7014'. The present botanical description is that of the variety at approximately 3 months old on Oct. 20, 2009 at 11:30 a.m. in a room under north light in Wimauma, Fla. The colors (except those in common terms) are described from R.H.S. Colour Chart published by The Royal Horticultural Society in London (1986 ed.), in association with the Flower Council of Holland.

DETAILED BOTANICAL DESCRIPTION

Classification:

*Botanical.*—*Gerbera hybrida* 'UFGE 7014'.

*Common Name.*—*Gerbera.*

Parentage:

*Female, or seed, parent.*—'Sunburst Snow White' (unpatented).

*Male, or pollen, parent.*—'UFGE 4033' (unpatented).

Inflorescence:

*Appearance.*—Semi-double type inflorescence form; solitary inflorescences borne on upright and strong scapes above the foliar plane; ray and disc florets arranged acropetally on a capitulum.

*Diameter.*—About 11 cm.

*Color* (*general tonality from a distance of* 3 *meters*).—Bright white (RHS 155D).

*Shape.*—Incurving funnel-shaped.

*Fragrance.*—None detected.

*Flowering season.*—Plants begin flowering about seven weeks after planting and flower year-round in outdoor gardens in Wimauma, Fla., until plants are killed by frosts or freezes; plants flower year-round under greenhouse conditions in Wimauma, Fla.

*Inflorescence longevity.*—Inflorescences last about two to three weeks on the plant in Wimauma, Fla.; inflorescences not persistent.

*Quantity of inflorescences.*—Free flowering habit, with up to 14 open and developing inflorescences per plant at one time.

*Inflorescence bud.*—Height: About 1.6 cm. Diameter: About 2.2 cm. Shape: Oblate. Color (opening buds): Close to yellow-green (RHS 154C).

*Inflorescence size.*—Diameter: About 11 cm. Depth (height): About 1.8 cm. Diameter of disc: About 2.3 cm. Receptacle height: About 4 mm. Receptacle diameter: About 1.5 cm. Receptacle color: Close to white (RHS 155B).

*Phyllaries.*—Number of phyllaries per inflorescence: About 62 arranged in about three whorls. Length: About 1.3 cm. Width: About 2 mm. Shape: Subulate. Apex: Narrowly acute. Base: Truncate. Margin: Entire. Texture, upper surface: Smooth, glabrous. Texture, lower surface: Moderately tomentose. Color, upper surface: Close to green (RHS 144A). Color, lower surface: Close to green (RHS 137C). Color, towards the base: Close to green (RHS 137B).

*Inner ray florets.*—Number per inflorescence: About 140 arranged in about three whorls. Length: About 2.2 cm. Width: About 2 mm. Shape: Narrow elliptic. Apex: Emarginate to obtuse. Base: Truncate. Margin: Entire. Texture, upper surface: Smooth, glabrous, slightly velvety. Texture, lower surface: Smooth, glabrous, slightly velvety. Color, upper surface: Close to white (RHS 155D). Color, lower surface: Close to white (RHS 155B).

*Outer ray floret.*—Number: About 57 arranged in three whorls. Cross section: Convex. Length: About 4.5 cm. Width: About 9 mm. Shape: Narrow elliptic. Apex: Emarginate to obtuse. Base: Truncate. Margin: Entire. Texture, upper surface: Smooth, glabrous, slightly velvety, longitudinally ridged. Texture, lower surface: Smooth, glabrous, slightly velvety, longitudinally ridged. Color, upper surface: White (RHS 155D). Color, lower surface: White (RHS 155B). Color distribution on inner side: Uniform. Edge of different color: None.

*Disc florets.*—Number: About 270. Length: About 1.5 cm. Width: About 3 mm. Shape: Tubular, fused. Apex: Narrowly obtuse. Base: Fused. Margin: Entire. Texture, upper and lower surfaces: Smooth, glabrous. Color, fully opened upper surface: Close to white (RHS 155B). Color, fully opened lower surface: Close to white (RHS 155B). Color, fully opened midsection: Close to white (RHS 155A). Color, fully opened base: Close to white (RHS 155B).

*Reproductive organs.*—Androecium: On disc floret only; quantity: one. Gynoecium: On both ray and disc florets; quantity per floret: one. Filament length: About 3 mm. Filament color: Close to white (155B). Anther shape: Linear. Anther length: About 4 mm. Anther width: About 1 mm. Anther color: Close to yellow (RHS 13A). Pollen: amount: Very scarce. Pollen color: Close to yellow (RHS 8B). Pistil: One per floret. Pistil length: About 1.6 cm. Stigma shape: Cleft. Stigma color: Close to white (RHS 155B). Style length: About 1.2 cm. Style color, distally and proximally: Close to white (155B). Ovary, color. Close to white (RHS 155A).

*Pappus.*—Quantity of hairs per floret: About 85. Length: About 6 mm. Diameter: Less than 1 mm. Texture: Soft. Color: Yellow-white (RHS 158D).

*Peduncle.*—Length: About 42 cm. Diameter: About 6 mm; distally, about 3.6 mm. Strength: Strong. Texture: Moderately densely tomentose. Color: Close to yellow-green (RHS 144B and 144C); distally, yellow-green (RHS 144D); proximally, red-purple (RHS 60B).

Plant:

*General appearance.*—Herbaceous perennial, typically grown as container or garden plants; upright and mounding growth habit, roughly globular in shape; leaves arranged in basal rosettes and outwardly arching; dense and bushy habit; inflorescences held above the foliar plane on erect and strong basal peduncles (or scapes); moderately vigorous.

*Plant height, soil level to top of foliar plane.*—About 30 cm.

*Plant height, soil level to top of inflorescence.*—About 45 cm.

*Plant width.*—About 62 cm.

*Foliage.*—Leaf blade: Length: About 26.5 cm. Width: About 14 cm. Shape: Oblong. Apex: Moderately acute to obtuse. Base: Truncate. Margin: Irregular crenate, sinuses divergent, undulate. Texture, upper surface: Sparsely pubescent. Texture, lower surface: Moderately pubescent. Venation pattern: Pinnate. Color, upper surface: Close to green (RHS 137A). Color, lower surface: Close to yellow-green (RHS 147B). Petiole: Length: About 7.5 cm. Diameter: About 4 mm. Texture, upper and lower surfaces: Moderately pubescent. Color, upper and lower surfaces: Close to yellow-green (RHS 144B and 144C), with blotches of brown (RHS 200A). Color, proximal end: Close to red-purple (RHS 60B and 60C).

Resistance to diseases: 'UFGE 7014' has been observed in multiple experiments in which it was compared with two common commercial cultivars, 'Pensacola' *gerbera* (unpatented) and 'Bimini' *gerbera* (unpatented), for the incidence and severity of powdery mildew, *Podosphaera* (syn. *Sphaerotheca*) *fusca* (Fr.) S. Blumer. 'UFGE 7014' has consistently been found to have a moderate level of resistance to powdery mildew. In two experiments conducted, Experiment 1 in winter 2008 and spring 2009, and Experiment 2 in summer and fall 2009, both at Wimauma, Fla., tissue culture liners of 'UFGE 7014', 'Bimini', and 'Pensacola' were transplanted on into 2.7-L containers filled with commercial potting mix amended with controlled release fertilizer at the rate of 5.28 $kg \cdot m^{-3}$ and trace element fertilizer at the rate of 1.05 $kg \cdot m^{-3}$. Plants were grown under a plastic tunnel within a screen house with approximately 45% light exclusion. Fungicides were not applied throughout the experiments to subject the plants to natural powdery mildew disease pressures. In Experiment 1, the severity of powdery mildew on *gerbera* leaves was assessed at week 8 after transplanting (Feb. 4, 2009), week 10 after transplanting (Feb. 18, 2009), week 12 after transplanting (Mar. 4, 2009), and week 14 after transplanting (Mar. 18, 2009). In Experiment 2, the severity of powdery mildew was assessed at week 8 after transplanting (Oct. 15, 2009), week 10 after transplanting (Oct. 29, 2009), and week 12 after transplanting (Nov. 12, 2009). A randomized complete block design was used with five replications in Experiment 1 and with eight replications in Experiment 2. The experimental unit was a single containerized plant. 'UFGE 7014' showed a moderate level of resistance to powdery mildew in both Experiment 1 and Experiment 2 (Table 1). 'UFGE 7014' remained to be more productive than 'Bimini' and 'Pensacola' when natural powdery mildew disease pressure existed (Table 1). No other disease resistance characterizations have been made.

TABLE 1

Powdery mildew severity ratings and flower counts of 'UFGE 7014' and two commercial gerbera cultivars, 'Bimini' and 'Pensacola', grown under natural powdery mildew pressure in two experimental trials in Wimauma, FL. Experiment 1 (Winter 2008 through Spring 2009), Experiment 2 (Summer 2009 through Fall 2009)

| | PM Ratings[Z] | | | | Inflorescence |
|---|---|---|---|---|---|
| Cultivars | Week 8 | Week 10 | Week 12 | Week 14 | counts[Y] |
| Experiment 1 (Winter 2008 through Spring 2009) | | | | | |
| 'UFGE 7014' | 1.2 | 2.2 | 4.2 | 6.6 | 5.6 |
| 'Bimini' | 1.2 | 1.8 | 5.4 | 8.0 | 3.2 |
| 'Pensacola' | 1.0 | 2.0 | 4.8 | 8.6 | 3.0 |
| Experiment 2 (Summer 2009 through Fall 2009) | | | | | |
| 'UFGE 7014' | 1.5 | 6.5 | 7.0 | | 4.3 |
| 'Bimini' | 2.6 | 8.6 | 9.4 | | 2.6 |
| 'Pensacola' | 1.8 | 7.5 | 9.8 | | 1.1 |

[Z]Powdery mildew severity was rated on a scale of 1 to 10 as described by Hausbeck et al. (2002): 1 = no disease, 2 = trace to 10%, 3 = 10% to 20%, 4 = 20 to 30%, 5 = 30% to 40%, 6 = 40% to 50%, 7 = 50% to 60%, 8 = 60% to 70%, 9 = 70% to 80%, and 10 = 80% to 100% of leaf surface covered with powdery mildew.
[Y]Total number of inflorescences produced per plant over nine weeks from Jan. 20, 2009 to Mar. 17, 2009 in Experiment 1 or from Sep. 25, 2009 to Nov. 20, 2009 in Experiment 2, both in a screen house in Wimauma, FL

COMPARISON WITH PARENTAL AND KNOWN CULTIVARS

'UFGE 7014' differs from the female parent 'Sunburst Snow White' (unpatented) by having larger leaves, longer peduncles, larger inflorescences, and stronger powdery mildew resistance under growing conditions in Wimauma, Fla. than 'Sunburst Snow White'. 'UFGE 7014' differs from the male parent 'UFGE 4033' (unpatented) by having more leaves, fuller plants, and more flowers under growing conditions in Wimauma, Fla. than 'UFGE 4033'.

Comparisons were made with the commercial *gerbera* variety 'Bimini' (unpatented) and the commercial *gerbera* variety 'Pensacola' (unpatented). Two experiments were conducted in a greenhouse in Wimauma, Fla. under standard greenhouse management practices to evaluate the plant performance (days to inflorescence, inflorescence quality, inflorescence count, and plant quality) of 'UFGE 7014' for container plant production in comparison to 'Bimini' and 'Pensacola'. In the first of the two plant performance experiments (Experiment 3), tissue culture liners were transplanted on Dec. 9, 2008 into 2.7-L containers filled with commercial potting mix amended with controlled release fertilizer at the rate of 5.28 $kg \cdot m^{-3}$ and trace element fertilizer at the rate of 1.05 $kg \cdot m^{-3}$. Potted plants were grown on metal benches in a glass house and spaced 46 cm×46 cm apart. Temperatures inside the greenhouse ranged from 18° C. to 33° C. Two hours of additional photoperiodic lighting were provided between Dec. 9, 2008 and Mar. 17, 2009. Fungicides and insecticides were applied as needed to control powdery mildew and western flower thrips. Inflorescence quality was rated on a 1 to 5 scale: 1=very poor, 3=fair, some blemishes, but acceptable, and 5=excellent, bright, uniform, and no blemishes. Inflorescence counts were recorded weekly from Jan. 20, 2009 through Mar. 17, 2009. Plant quality was rated three times, on Jan. 20, 2009, Feb. 3, 2009, and Feb. 17, 2009, using a 1 to 5 scale: 1=few leaves or long petioles, container surface visible, very poor and unacceptable as flowering pot plants, 3=fair and marketable, and 5=excellent, full, symmetrical, attractive plants.

In the second of the two plant performance experiments (Experiment 4), tissue culture liners were transplanted on Aug. 13, 2009 into 2.7-L plastic containers filled with commercial potting mix amended with controlled release fertilizer at the rate of 5.28 $kg \cdot m^{-3}$ and trace element fertilizer at the rate of 1.05 $kg \cdot m^{-3}$. Plants were grown on metal benches in a greenhouse with a spacing of 46 cm×46 cm. The greenhouse was covered with aluminum shading cloth with approximately 30% light exclusion. Greenhouse temperatures ranged from 21° C. to 35° C. Two hours of additional photoperiodic lighting was provided beginning Sep. 15, 2009. Fungicides and insecticides were applied as needed to control powdery mildew and western flower thrips. Inflorescence quality and plant quality were rated as above for Experiment 3, but on Sep. 25, 2009, Oct. 15, 2009, and Nov. 5, 2009. The number of flowers produced per plant was recorded weekly from September 25, 2009 through Nov. 20, 2009.

The experiment design for the plant performance experiments was a randomized complete block design with five replications in Experiment 3 and eight replications in Experiment 4. The experimental unit was a single containerized plant.

'UFGE 7014' came into flowering 14 to 19 days earlier than 'Bimini' and 'Pensacola' in Experiment 3 and 7 to 13 days earlier than 'Bimini' and 'Pensacola' in Experiment 4 (Table 2). Inflorescence quality ratings of 'UFGE 7014' were 5.0 to 4.7, similar to that of 'Bimini' (5.0 to 4.8), and higher than that of 'Pensacola' (4.1 to 4.3) (Table 2). In both Experiment 3 and Experiment 4, 'UFGE 7014' produced more inflorescences (253% to 163% more than 'Bimini' and 543% to 360% more than 'Pensacola') (Table 2). The plant quality rating of 'UFGE 7014' was 4.7 in both Experiment 3 and Experiment 4, higher than that of the controls (Table 2).

TABLE 2

Plant performance of 'UFGE 7014' and two commercial cultivars, 'Bimini' and 'Pensacola' grown in Experiment 3 (Winter 2008 through Spring 2009) and Experiment 4 (Summer 2009 through Fall 2009) in Wimauma, Florida.

| Cultivars | Days to 1st open inflorescences (no.) | Inflorescence quality[Z] | Inflorescence counts[Z] (no.) | Plant quality[Y] |
|---|---|---|---|---|
| Experiment 3 (Dec. 9, 2008 to Mar. 17, 2009) | | | | |
| 'UFGE 7014' | 49.6 | 5.0 | 7.6 | 4.7 |
| 'Bimini' | 64.0 | 5.0 | 3.0 | 3.1 |
| 'Pensacola' | 68.8 | 4.1 | 1.4 | 3.3 |

TABLE 2-continued

Plant performance of 'UFGE 7014' and two commercial cultivars, 'Bimini' and 'Pensacola' grown in Experiment 3 (Winter 2008 through Spring 2009) and Experiment 4 (Summer 2009 through Fall 2009) in Wimauma, Florida.

| Cultivars | Days to 1st open inflorescences (no.) | Inflorescence quality[Z] | Inflorescence counts[Z] (no.) | Plant quality[Y] |
|---|---|---|---|---|
| Experiment 4 (Aug. 13, 2009 to Nov. 20, 2009) | | | | |
| 'UFGE 7014' | 42.3 | 4.7 | 9.0 | 4.7 |
| 'Bimini' | 50.1 | 4.8 | 5.5 | 3.2 |
| 'Pensacola' | 55.8 | 4.3 | 2.5 | 3.3 |

[Z]Inflorescence count data were collected over nine weeks from Jan. 20, 2009 to Mar. 17, 2009 in Experiment 3 and another nine weeks from Sep. 25, 2009 to Nov. 20, 2009 in Experiment 4. Each value represents the mean of five (Experiment 3) or eight (Experiment 4) replicates.

[Y]The plant quality rating value in Experiment 3 was the mean of five replicates over three times (January 20, February 3, and Feb. 17, 2009), and the plant quality rating value in Experiment 4 was the mean of eight replicates over three times (September 25, October 15, and Nov. 5, 2009).

Literature Cited

Hausbeck, M. K., W. R. Quackenbush, and S. D. Linderman. 2002. Evaluation of cultivars of African daisy for resistance to powdery mildew, 2002. B&C Tests 18:O0004.

We claim:

1. A new and distinct cultivar of *Gerbera* plant named 'UFGE 7014', as illustrated and described herein.

* * * * *